United States Patent [19]
Johnson et al.

[11] Patent Number: 5,171,693
[45] Date of Patent: Dec. 15, 1992

[54] METHOD FOR THE DETERMINATION OF N-METHYL-2-PYRROLIDONE (NMP) CONTENT IN POLYIMIDE RESIN PRE-IMPREGNATED FABRIC

[75] Inventors: Sean A. Johnson; Nancy K. Roberts, both of Chino, Calif.

[73] Assignee: General Dynamics Corporation Air Defense Systems Division, Pomona, Calif.

[21] Appl. No.: 726,268

[22] Filed: Jul. 5, 1991

Related U.S. Application Data

[63] Continuation of Ser. No. 201,820, Jun. 3, 1988, abandoned.

[51] Int. Cl.$^5$ .............................................. G01N 33/44
[52] U.S. Cl. ........................................ 436/85; 422/78; 436/128; 436/157; 436/161
[58] Field of Search .................... 422/78, 89, 82.12; 436/85, 128, 147, 155, 157, 161

[56] References Cited
U.S. PATENT DOCUMENTS

| | | |
|---|---|---|
| 3,169,389 | 2/1965 | Green, Jr. et al. |
| 3,171,274 | 3/1965 | Loyd |
| 3,171,722 | 3/1965 | Natelson |
| 3,305,000 | 2/1967 | Bullen et al. ............... 436/161 |
| 3,372,573 | 3/1968 | Sanford et al. |
| 3,407,647 | 10/1968 | Lynn |
| 3,623,843 | 11/1971 | Brownlee ................... 422/89 |
| 3,779,066 | 12/1973 | Fore et al. |
| 3,889,538 | 6/1975 | Fingerle |
| 3,895,915 | 7/1975 | Haldeman ................... 422/88 |
| 3,996,003 | 12/1976 | Fine et al. |
| 4,006,411 | 3/1978 | Fine et al. ................... 422/89 |
| 4,081,345 | 3/1978 | Tölg et al. ................... 422/82.01 |
| 4,335,620 | 6/1982 | Adams |
| 4,452,067 | 6/1984 | Ahlstrom, Jr. et al. |

OTHER PUBLICATIONS

"Gas Chromatographic Estimation of Occluded Solvents in Adhesive Tape by Periodic Induction Method" by M. Suzuki Analytical Chemistry, vol. 42, No. 14, Dec., 1970, pp. 1705-1708.

"Analysis of Fixed and Condensable Gases by Two-Stage Gas Chromatography" by J. Madison Analytical Chemistry, vol. 30, No. 11, Nov., 1958, pp. 1859-1862.

"Gas Chromatography of Volatiles from Breath and Urine" by R. Teranishi et al Analytical Chemistry, vol. 44, No. 1, Jan., 1972, pp. 18-20.

"An Injection System for Gas Chromatography" by W. W. Nawar et al, Analytical Chemistry vol. 32, No. 11, Oct., 1960, pp. 1534-1535.

*Primary Examiner*—Jill A. Johnston
*Attorney, Agent, or Firm*—Henry Bissell; Leo R. Carroll

[57] ABSTRACT

A method is presented for the accurate quantitative determination of amounts of reactive (water and ethanol) and non-reactive N-methyl-2-pyrrolidone (NMP) volatiles in graphite-polyimide prepreg samples. The method is also applicable to other condensation-curing and/or solvent-impregnated prepreg systems, regardless of the type of reinforcement. Prepreg samples are heated in a containment chamber and the volatiles are subsequently flushed from the chamber with dry nitrogen gas. The volatiles are condensed, weighed, and analyzed via gas chromatography to determine the volatile composition. The method offers a means of purging the extremely tightly held, relatively non-volatile NMP solvent from the resin matrix by means of high temperatures applied to the sample chamber. The higher volatility reaction products are also captured by means of the specially designed very low temperature condenser. An internal check (collection efficiency) on the accuracy of the results is included in the test method. The method has been expressly designed for application to routine quality control situations.

9 Claims, 1 Drawing Sheet

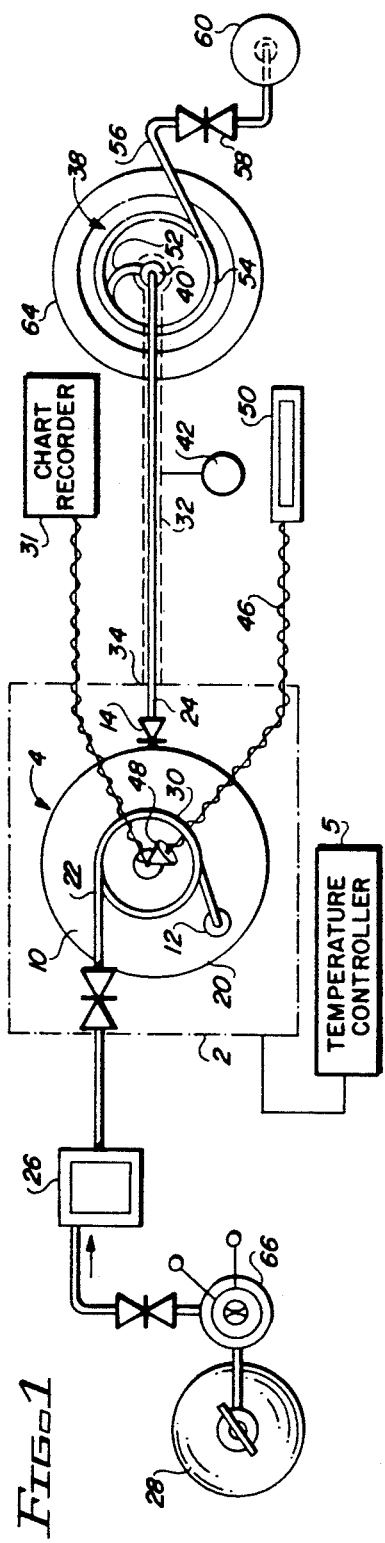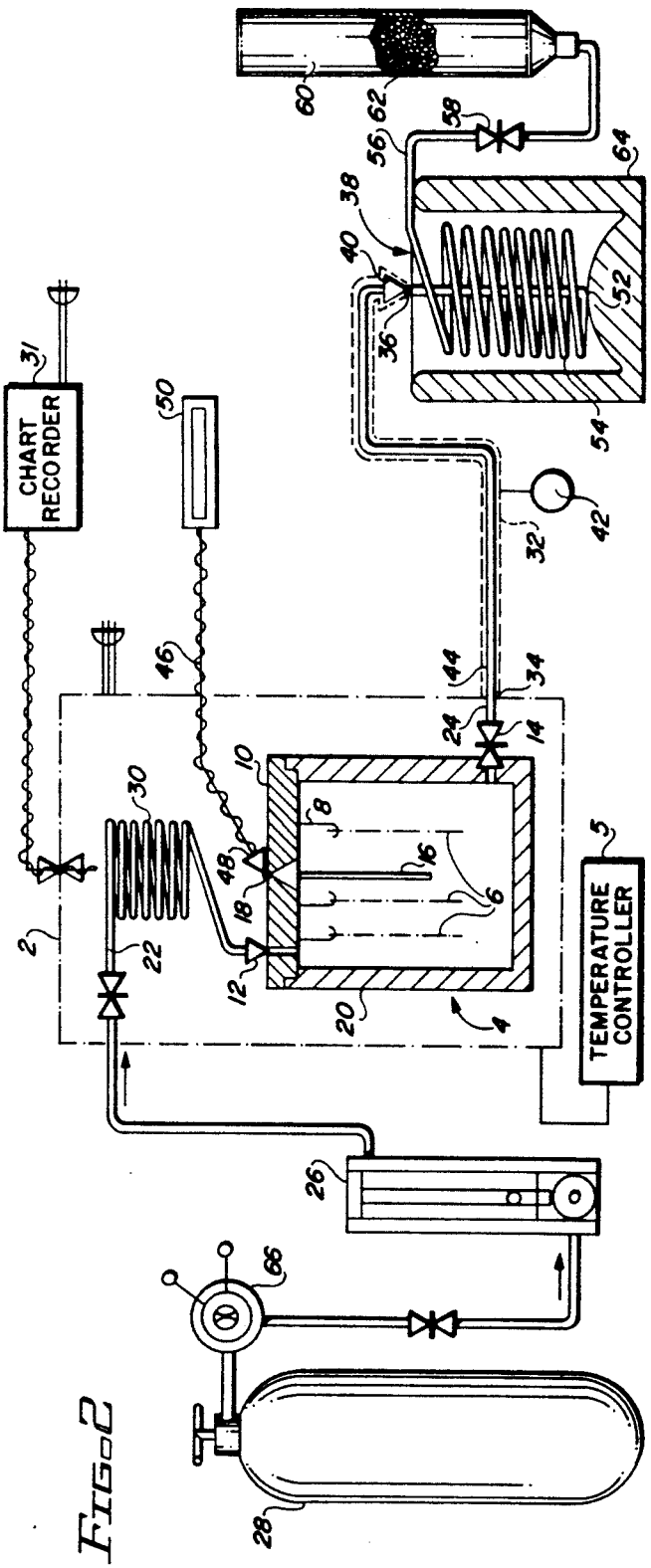

5,171,693

METHOD FOR THE DETERMINATION OF N-METHYL-2-PYRROLIDONE (NMP) CONTENT IN POLYIMIDE RESIN PRE-IMPREGNATED FABRIC

This invention was made with Government support under Contract No. N0024-85-C-5501 awarded by the U.S. Navy. The Government has certain rights in this invention.

This is a continuation, of application Ser. No. 07/201,820, filed Jun. 3, 1988, now abandoned.

RELATED APPLICATIONS

This application is related to two other applications which are being filed concurrently herewith, entitled: "Sample Containment Chamber, Corrosion Resistant Steel, Gas Tight," by Sean A. Johnson et al; and "Condenser, Hermetic Sealing, High and Low Temperature Resistant," by Sean A. Johnson et al, both assigned to the assignee of the present application. The inventions of those applications are subject to the same rights clause set forth above.

BACKGROUND OF THE INVENTION

1. Field of the Invention.

This invention relates to apparatus and methods for quantitatively determining the amount of volatile products and solvents remaining in a material after manufacture and, more particularly, to determining the amount of the specific solvent N-methyl-2-pyrrolidone (NMP) in resin pre-impregnated fabric ("prepreg").

2. Description of the Related Art.

In the present context, pre-impregnation refers to the coating of a reinforcing material or substrate with a resin before molding takes place. "Prepreg" is a term for the reinforcing material that contains or is combined with the full complement of resin before the molding operation.

Gas chromatography is a method of separating and analyzing mixtures of liquid or gaseous chemical substances by adsorption, which is a preferential adsorption of specific chemical compounds (in the gas phase) onto a solid or solid-liquid adsorbent material to achieve separation of components present therein.

Previously it has not been possible to monitor the amount of high-boiling-point solvent NMP present in polyimide impregnated fabric. Heretofore the volatile content tests that have been performed have evolved reactive volatiles (specifically ethanol and water) plus a variable amount of the non-reactive volatiles (NMP) present.

The amount of solvent retained in prepreg after manufacture is a critical parameter which directly affects the success of subsequent operations to produce finished parts from the prepreg. The art associated with test methods in the areas of process and quality control for solvated condensation-curing resin prepregs would be greatly benefited by a test method which evolves all reactive and non-reactive volatiles from prepreg test specimens and permits quantitative analysis of the amounts of individual chemical species in the condensate. It would also be valuable if such a test method included an internal check on collection efficiency to insure that the results obtained were accurate. Such a test method would provide a basis for determination of the levels of reactive and non-reactive volatiles retained in other solvated condensation-curing resin systems employing other solvents (e.g., methanol, ethanol, benzene, toluene, xylene, diglyme, etc.) as well as other types of condensation-curing resin systems (e.g., phenolics, various other polyimides, polybenzimidazoles, etc.).

General background information about gas chromatography and examples of the related art are given in the following U.S. patents and other publications.

U.S. Pat. No. 3,169,389 to Green, Jr. et al describes a method and means for gas chromatographic analysis adapted to resolve a sample mixture into fractions having similar boiling points.

U.S. Pat. No. 3,171,274 to Loyd describes a method and apparatus for gas chromatographic analysis entailing a vaporizing and sampling method for analysis of a liquid which normally tends to polymerize upon heating.

U.S. Pat. No. 3,171,722 to Natelson describes a gas extractor and ejector for use in gas chromatography which provide an arrangement for the separation of gases and liquids. Precise quantities of gases are fed to a gas chromatograph device to analyze very small quantities of gas. Samples of consistent quantity and volume are provided with the objective of obtaining consistent results on a gas chromatograph device.

U.S. Pat. No. 3,372,573 to Sanford et al describes a method and apparatus for chromatographic analysis comprising a valving system with three sequentially operating control units to provide an improved method and apparatus for obtaining a vaporous sample from a liquid containing a soluble non-volatile constituent.

U.S. Pat. No. 3,407,647 to Lynn describes a system which provides a vaporized sample to a gas chromatography column via a vaporizing chamber into which the sample is forced under high pressure, then vaporized and carried into the column by a low-pressure carrier gas.

U.S. Pat. No. 3,779,066 to Fore et al describes a method and means for gas chromatographic analysis of residual solvents and acetone dimers in oil seed meals and flours.

U.S. Pat. No. 3,889,538 to Fingerle describes a method and means for introducing a small sample of a volatile liquid into the carrier gas stream of a gas chromatography unit.

U.S. Pat. No. 3,996,003 to Fine et al describes a liquid chromatograph system for detecting N-nitroso compound content in specific samples.

U.S. Pat. No. 4,335,620 to Adams describes a temperature controlled sample carrier apparatus suitable for use in liquid chromatography systems.

U.S. Pat. No. 4,452,067 to Ahlstrom, Jr., et al describes a method and means for gas chromatographic vapor phase analysis of process streams containing condensible and non-condensible phases variously comprising hydrogen, water, oxides of carbon, aliphatic hydrocarbons, and aromatic hydrocarbons.

The article "An Injection System For Gas Chromatography" by Nawar et al in Analytical Chemistry, Volume 32, No. 11, October, 1960, describes a sample volatilization and injection system for a gas chromatography unit.

The article "Gas Chromatography of Volatiles From Breath And Urine" by Teranishi et al in Analytical Chemistry (USA), Volume 44, No. 1, Jan. 1972, describes a technique for gas chromatographic analysis of volatiles from human breath and urine.

The article "Analysis of Fixed And Condensible Gases by Two-Stage Gas Chromatography" by Madison in Analytical Chemistry, Volume 30, No. 11, Nov. 1958, describes a two-stage gas chromatographic analysis method for mixtures of fixed and condensible gases.

The article "Gas Chromatographic Estimation of Occluded Solvents in Adhesive Tapes by Periodic Introduction Method" in Analytical Chemistry (USA), Volume 42, No. 14, Dec. 1970, by Suzuki describes a method and apparatus for gas chromatographic analysis of occluded solvents in coated materials such as adhesive tape via a vaporizing attachment connected to the inlet port of a gas chromatographic unit.

SUMMARY OF THE INVENTION

The present invention allows the accurate quantitative measurement of amounts of reactive (water and ethanol) and non-reactive volatiles (NMP) in graphite-polyimide prepreg samples. A method is presented which is also applicable to other condensation-curing and/or solvent-impregnated prepreg systems, regardless of the type of reinforcement. Prepreg samples are heated in a containment chamber and the volatiles are subsequently flushed from the chamber with dry nitrogen gas. The volatiles are condensed, weighed, and analyzed via gas chromatography to determine the volatile composition. The method offers a means of purging the extremely tightly held, relatively non-volatile NMP solvent from the resin matrix by means of high temperatures applied to the sample chamber. The higher volatility reaction products are also captured by means of the specially designed very low temperature condenser. An internal check (collection efficiency) on the accuracy of the results obtained is included in the test method. The method has been expressly designed for application to routine quality control situations.

BRIEF DESCRIPTION OF THE DRAWINGS

A better understanding of the present invention may be realized from a consideration of the following detailed description, taken in conjunction with the accompanying drawing in which:

FIG. 1 is a schematic diagram showing a plan view of one particular arrangement of the present invention; and FIG. 2 is a schematic diagram showing an elevational view of the apparatus of FIG. 1.

DESCRIPTION OF THE PREFERRED EMBODIMENT

In accordance with the present invention, a method and apparatus are presented for determining the amount of solvent NMP retained in prepreg after manufacture. The method of testing NMP content is designed to measure amounts of reactive volatiles (water and ethanol) and non-reactive volatiles NMP. The method is carried out by heating prepreg samples in a containment chamber and flushing the volatiles from the chamber with dry nitrogen gas. The volatiles are condensed, weighed, and analyzed via gas chromatography (GC) to determine volatile composition. The weight of condensed volatiles collected is compared against the weight lost by the contained prepreg samples as a check of the accuracy and efficiency of each individual analysis.

As indicated by FIGS. 1 and 2, the apparatus consists of the following components and materials.

Oven

A circulating air oven 2 with a minimum temperature capability of 427° C. (800° F.) and access for gas inlet and outlet lines and an auxiliary thermocouple probe is used. The oven interior has sufficient volume to fully enclose a sample containment chamber 4 and all associated inlets and outlets. A controller 5 is used to control the temperature of the oven interior.

Sample Containment Chamber

The sample containment chamber 4 has the capacity to fully contain test samples 6 and all volatile products evolved during the course of the test. That is, the chamber 4 is capable of gastight operation. The chamber 4 should have a maximum internal volume of 1966 cubic centimeters (120 cubic inches). Samples 6 are enclosed and suspended in the chamber 4 in such a manner that no sample is closer than 0.5 inches to any chamber wall and the samples are a minimum of 0.8 inches apart from each other when suspended. The samples 6 are suspended from hangers 8 mounted in the lid 10 of the chamber. Blind holes are used to locate the hangers; no through holes are allowed.

The chamber 4 is constructed of corrosion resistant steel with a nominal thickness of ⅛ inch. The gas inlet 12, gas outlet 14, and thermocouple 16 mounting fittings are also of corrosion resistant steel. The walls and bottom of the chamber are seam welded inside and outside.

The gas inlet 12 is in the lid 10 of the chamber 4 near one edge. The gas outlet 14 is located on a wall area opposite from the gas inlet side near the bottom of the wall. The thermocouple probe mounting 18 is located in the lid 10 so that the thermocouple probe 16 when positioned within the chamber 4 is midway between two of the samples 6 without touching the samples. The thermocouple probe 16 extends approximately to one-half the depth of the chamber 4.

The chamber 4 is sealed either by means of a gasket or an O-ring (not shown) mounted between the lid 10 and the body 20 of the chamber. The material for construction of the seal is high-temperature silicone elastomer postcured for 60+/−15 minutes at 316°+/−6° C. (600°+/−10° F.) in a circulating air oven. No organic material is used in any other location within the containment chamber 4. A seal is used only once and then discarded.

Inlet and Outlet Lines

The inlet and outlet lines 22, 24 are made of corrosion-resistant steel with connectors capable of assuring leak-free connections to all fittings. If necessary, fluoroplastic pipe dope is used at line connections to fittings to assure leak-free operation.

A 0–50 ml per minute gas flow meter 26 is attached between a nitrogen gas bottle 28 and the point at which the inlet line 22 enters the oven 2. Before the point at which the inlet line 22 enters the sample containment chamber 4, 13+/−2 feet of the inlet line 22 are coiled inside the oven to form a pre-heating environment 30 for the nitrogen gas which is fed to the chamber. A thermocouple-strip chart recorder 31 is shown adjacent the preheater 30 to monitor chamber temperature.

The outlet line 24 is wrapped with a resistively heated tape 32 from the point 34 at which it leaves the oven 2 to the point of connection 36 with a condenser 38. The heating tape 32 extends to a condenser inlet valve 40 and makes at least one full turn around the valve body to ensure that frozen condensate does not plug the inlet valve 40.

The heating tape 32 is heavy glass-insulated tape, suitable for direct contact with metal, ½ inch wide by 8 feet long and rated for continuous operation at 316° C. (600° F.) or greater. A suitable tape is manufactured by Thermolyne and available from Fisher Scientific as P/N 11-463-50D. The heating tape 32 is operated through a variable transformer 42 so that the level of heating can be controlled. The heating tape 32 is overwrapped with woven glass fabric 44 to insulate the line 24 and provide more even heat distribution.

Thermocouple Assembly

The thermocouple probe 16 is of the chromel-alumel type, with a corrosion resistant steel sheath ⅛ inch (nominal) diameter utilizing an exposed junction. A suitable thermocouple probe is manufactured by Omega Engineering, Inc., Stamford, Connecticut, and designated TJ36-CASS-18E-6-RP.

The probe mounting 18 is a compression fitting made of corrosion resistant steel which permits periodic removal of the thermocouple assembly for servicing but assures leak-free operation between the mounting 18 and containment chamber lid 10 and between the mounting 18 and the probe body 16. A suitable probe mounting 18 is manufactured by Omega Engineering, Inc., Stamford, Conn., and designated SSLK-18-14.

The thermocouple probe 16 and wire 46 are equipped with a chromel-alumel ceramic thermocouple connector 48 which permits quick disconnection of the probe 16 from the thermocouple wire 46 and associated readout 50 and remains viable for continuous operation at temperatures to 427° C. (800° F.). A suitable connector is manufactured by Omega Engineering, Inc., Stamford, Conn., and designated NHX-K-MF.

The thermocouple connector 48 is rigidly mounted to the probe 16 with a corrosion resistant steel compression fitting-connector adaptor. A suitable adaptor is manufactured by Omega Engineering, Inc., Stamford, Conn., and designated X-BRLK-18-NHX. The thermocouple wire 46 is glass insulated chromel-alumel.

Condenser

The condenser 38 is constructed from ¼ inch outside diameter (nominal), thin-walled copper tubing. The condenser has a straight vertical portion 52 of 6+/−1 inches at the inlet. From the bottom of the vertical section 52 the tubing is formed into an ascending coil 2.0+/−0.5 inches in diameter with a total of ten turns 54. The outlet segment 56 is 6+/−1 inches long and extends from the last coil roughly perpendicular to the vertical inlet segment 52.

The condenser 38 is equipped with inlet and outlet valves 40, 58. The inlet valve 40 is a corrosion resistant steel bellows-type valve. A suitable such valve is available from Arcadia Valve & Fitting Company, Arcadia, Calif., manufactured by Nupro Corp. and designated SS-4H. The outlet valve 58 is a brass plug type valve with fluoroplastic coated fluoroelastomer seals. A suitable outlet valve is manufactured by Nupro Corp., designated B-4P4T, and available from Arcadia Valve & Fitting Company, Arcadia, Calif.

A drying tube 60 is installed downstream from the condenser outlet valve 58 to prevent atmospheric moisture from entering the condenser 38. The drying tube 60 is filled with an indicator-type granulated desiccant 62 such as Dri-Rite.

Gas Chromatograph

A gas chromatograph unit equipped with programmable gradient temperature capability, a thermal conductivity detector, and an electronic integrator output is utilized. The gas chromatograph unit utilizes a Tenax GC 60/80 mesh packed column six feet long with ⅛ inch outside diameter, which is available from Alltex Associates, Inc., Deerfield, Ill., and designated 4900 PC.

Miscellaneous Equipment

The following items of miscellaneous equipment are needed:

A square metal template 4.00+/−0.12 inches on a side, an analytical balance accurate to 0.01 grams with a minimum capacity of 1000 grams, a Dewar flask 64 large enough to completely contain the condenser coil 54, a laboratory thermometer marked in increments of 1° C. (2° F.) and capable of measuring temperatures down to −78° C. (−110° F.), an analog-to-digital thermocouple readout converter 50, and 1.0 microliter gas chromatography syringe equipped with a Chaney adaptor.

Reagents

The following reagents are needed: dry, ultra high-purity (99.99%) helium gas; dry nitrogen gas (99.9% or better purity); technical grade isopropyl alcohol (IPA); dry ice ($CO_2$); technical grade methylene chloride; deionized water; absolute ethanol; and reagent grade NMP.

Method of Operation

Using the template described above under "Miscellaneous Equipment," three specimens 6 of prepreg are cut on the bias approximately equidistant across the fill direction of the prepreg and a minimum of 3 inches from each selvage edge. The samples 6 are weighed to the nearest 0.01 gram and the combined weight is recorded as "A."

The cleaned and dried condenser 38 is weighed to the nearest 0.01 gram and the weight is recorded as "B."

The prepreg samples 6 are suspended from three hooks 8 in the containment chamber lid 10 using wire. Care is taken to see that no fibers are lost from the samples 6 and that they do not come into contact with each other or any wall of the containment chamber.

The cleaned and dried containment chamber 4 is assembled. The chamber lid 10 is carefully attached to the chamber body 20 with the silicone gasket or O-ring in place and secured tightly.

The containment chamber 4 is placed into the oven 2 at ambient temperature. The gas inlet line 22 is attached to the assembled containment chamber 4 and so is the outlet line 24. The condenser 38 is secured to the end of the outlet line 24. The containment chamber thermocouple 16 is connected to the thermocouple wire 46 which in turn is connected to the digital readout 50. The operation of the thermocouple 16 is checked before proceeding further.

The condenser valves 40, 58 are opened and the nitrogen flow is set to 50 ml per minute by adjusting regulator 66 on nitrogen tank 28. All line connections, fittings on the containment chamber 4, and the seal between the lid 10 and body 20 of the containment chamber 4 are leak tested using a bubble leak test. If any leaks are detected, they are fixed before proceeding further.

The nitrogen flow rate is reduced to 20-25 ml per minute. Power is applied to the outlet line heating tape 32 and the variable transformer 42 is adjusted to give temperatures on the outlet line 24 surface of 274°+/−14° C. (525°+/−25° F.). The Dewar flask 64 is set up around the condenser 38 and finely crushed dry ice is added to cover the condenser coil 54. Isopropyl alcohol is slowly added with stirring to make a thick slurry. The slurry is maintained at or below a temperature of −73° C. (−100° F.) throughout the entire procedure; all the turns of the coil 54 are kept covered by the slurry. The temperature can be maintained by adding dry ice as necessary.

The set point of the oven controller 5 is set for 385°+/−5° C. (725°+/−10° F.). The oven power and air circulation fan are then turned on. The nitrogen flow rate must remain between 20 and 25 ml per minute.

When the sample containment chamber thermocouple 16 reaches 316° C. (600° F.), the oven controller 5 setpoint is reduced as required to hold the temperature of the chamber interior at 321°+/ −5° C. (610°+/−10° F.) for 35+/−5 minutes.

At the end of the temperature holding period the oven heater is turned off but the oven fan is left running with the oven door closed. The nitrogen flow rate is turned up to 50+/−5 ml per minute and an additional 35+/−5 minutes of time is allowed to elapse.

Next the condenser inlet and outlet valves 40, 58 are closed in that order. The nitrogen gas flow is turned off. Power to the heating tape 32 is turned off and the tape 32 is removed from the condenser inlet valve 40. When the inlet valve 40 is cool enough to touch, the condenser 38 is removed from the system.

The condenser 38 is brought to ambient temperature and dried thoroughly. The condenser 38 is weighed to the nearest 0.01 gram and the weight is recorded as "C".

When the containment chamber 4 is cool enough to touch, it is disassembled and the test samples 6 are removed. The samples 6 are weighed to the nearest 0.01 gram and the combined weight is recorded as "D." Care is taken during the disassembly and subsequent cleaning of the containment chamber 4 not to damage the sealing surfaces. Care is also taken not to damage the samples 6 during disassembly of the chamber 4 and their removal from the chamber.

The liquid condensate from the condenser 38 is decanted into a 5 ml test tube and sealed immediately with natural cork or Para-film to prevent escape of condensate vapors. The contents of the condenser 38 are under pressure, so that the valve must be opened slowly while directing the flow from the valve into the test tube and away from any personnel.

The condenser 38 is cleaned by flushing it out with methylene chloride, blowing it out with clean dry air, and placing the condenser 38 under vacuum for 60+/−10 minutes. The inside of the containment chamber 4 is cleaned by wiping it with a cloth moistened with methylene chloride and then drying it with air. The desiccant in the drying tube is changed every third run.

GC Analysis of Condensate

The injector and detector temperatures are set to 235° C. (455° F.). The column oven is programmed as follows: initial temperature of 85° C. (185° F.), a 7-minute hold period, a ramp to 210° C. (410° F.) at 30° C. (54° F.) per minute, and a holding period of 6.5 minutes. The approximate retention times are: water, 1.12 minutes; ethanol, 5.00 minutes; NMP, 14.18 minutes.

The column is standardized as follows: a standard solution of 70.00+/−0.05 weight percent reagent grade NMP, 15.00+/−0.05 weight percent absolute ethanol, and 15.00+/−0.05 weight percent deionized water is prepared. The individual weight percents of the standard solution are recorded to the nearest 0.01%. Using a 1.0 microliter GC syringe with a Chaney adaptor, 0.3 microliters of the standard solution is injected into the GC. The standard solution is flushed and ejected at least five times and excess solution is wiped off the needle prior to injection. The temperature program is started at injection. The integrated area output for each standard component is recorded to the nearest 0.01%. The standardization procedure is repeated and instrument response factors are adjusted as necessary until a relative difference for each component between successive runs deviates by no more than 2%. The GC unit is standardized prior to each condensate analysis.

The condensate is analyzed as follows: using a 1.0 microliter GC syringe with a Chaney adaptor 0.3 microliters of the condensate is injected into the GC. The condensate solution is flushed and ejected at least five times and excess solution is wiped off the needle prior to injection. The temperature program is started at injection. The integrated area output for each component to the nearest 0.01% is recorded. Two runs are performed and the average weight percent of NMP is recorded as "E."

Calculations

The average weight percent of NMP in the uncured prepreg resin (NMP content) is calculated with the following equation:

$$\text{NMP content} = (E(C-B)/(AF)) \text{ times } 10{,}000$$

The collection efficiency (percent) is calculated as follows:

$$\text{Collection efficiency} = ((C-B)/(A-D)) \text{ times } 100$$

where A, B, C, D, and E are defined above and F is the average percent of resin content of the prepreg roll (not determined as part of this method). Note that collection efficiencies outside the range of 100.0+/−5.0% indicate excessive escape of volatile components or excessive contamination from outside sources. If collection efficiencies outside the acceptable range occur, the procedure should be repeated.

Commercial Applications

The test method described above permits the reliable monitoring of the level of solvent NMP retained in the prepreg after manufacture. This is a critical parameter which directly affects the success of subsequent operations which produce finished parts from the prepreg. The method of the present invention will have a significant role in the areas of process and quality control for solvated condensation-curing resin prepregs.

Although there have been described above an apparatus and method for the determination of NMP content in polyimide resin pre-impregnated fabric in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A method of determining the amounts of solvents retained in a material after manufacture, comprising the following steps in sequence:
   a) obtaining specimens from said material and determining the combined weight of said specimens;
   b) cleaning and drying a condenser having an inlet valve and an outlet vlave and determining the weight of said condenser;
   c) suspending said specimens from an interior side of a containment chamber lid;
   d) assembling a clean and dry containment chamber having a gas inlet line connected to a source of nitrogen gas and a gas outlet line attached thereto by putting said lid on the chamber with said specimens inside;
   e) placing said containment chamber in an oven at ambient temperature;
   f) securing said condenser inlet valve to a free end of sid outlet line of said containment chamber;
   g) connecting a thermocouple inside said containment chamber to an external readout;
   h) opening said inlet valve and said outlet valve on said condenser and setting a nitrogen gas flow through said containment chamber to a first predetermined flow rate;
   i) leak testing said containment chamber and associated valves and connections and a seal of said lid to said containment chamber and eliminating and leaks discovered;
   j) reducing said nitrogen flow rate to a second predetermined flow rate;
   k) heating said condenser inlet valve and said gas outlet line from said containment chamber to said condenser to a first predetermined temperature;
   l) cooling said condenser to a second predetermined temperature;
   m) setting said oven to a third predetermined temperature;
   n) reducing said third predetermined temperature of said oven to reach a fourth predetermined temperature as indicated by said thermocouple and holding it for a first predetermined time interval;
   o) turning off powder to said oven and increasing said nitrogen flow rate to said first predetermined flow rate for a second predetermined time interval;
   p) closing said inlet valve and said outlet valve of said condenser in that order and turning off said nitrogen gas flow;
   q) removing heat from said containment chamber outlet line and from said condenser inlet valve;
   r) removing said condenser from the outlet line of said containment chamber;
   s) drying said condenser thoroughly and recording the weight thereof with liquid condensate inside;
   t) disassembling said containment chamber and removing said specimens;
   u) weighing said specimens and recording the combined weight of said specimens;
   v) decanting a liquid condensate from said condenser into a container and sealing said container immediately; an
   w) subsequently withdrawing a portion of the liquid condensate from said container for gas chromatographic analysis.

2. The method of claim 1 wherein said solvents include N-methyl-2-pyrrolidone and said material comprises polyimide resin pre-impregnated fabric.

3. The method of claim 1 further comprising the step of calculating a collection efficiency from the weight values measured in steps a), b), s), and u).

4. The method of claim 3 wherein the step of calculating a collection efficiency comprises entering said weight values in the following equation:

$$\text{collection efficiency} = [(C-B)/(A-D)] \times 100$$

where A = the initial combined weight of the specimens, B = the initial weight of the cleaned and dried condenser of step b), C is the weight of the condenser and contained condensate of step s), and D is the combined weight of said specimens after the method of claim 1 has been performed; and performing the calculations indicated in said equation.

5. The method of claim 1 further comprising the steps of calculating the average weight percent of solvents retained in said specimens using the weight values determined in steps a), b), s), and u), and using a predetermined value for the average percent resin content of said material.

6. The method of claim 1 in which step b) is carried out by flushing said condenser with methylene chloride, blowing out said condenser with clean dry air, and placing said condenser under vacuum for about an hour.

7. The method of claim 1 in which said first predetermined flow rate of nitrogen in step h) is about 50 ml per minute and said second predetermined flow rate in step k) is 20 to 25 ml per minute.

8. The method of claim 1 wherein step l) is carried out by immersing said condenser in a slurry of dry ice and isopropyl alcohol.

9. The method of claim 1 further including the step of maintaining said specimens separate from each other and from the walls of said containment chamber after step c) is performed.

* * * * *